United States Patent
Fukuyama

(10) Patent No.: US 7,539,335 B2
(45) Date of Patent: May 26, 2009

(54) IMAGE DATA PROCESSOR, COMPUTER PROGRAM PRODUCT, AND ELECTRONIC ENDOSCOPE SYSTEM

(75) Inventor: Mitsufumi Fukuyama, Saitama (JP)

(73) Assignee: Hoya Corporation, Tokyo (JP)

( * ) Notice: Subject to any disclaimer, the term of this patent is extended or adjusted under 35 U.S.C. 154(b) by 718 days.

(21) Appl. No.: 11/329,103

(22) Filed: Jan. 11, 2006

(65) Prior Publication Data

US 2006/0152581 A1   Jul. 13, 2006

(30) Foreign Application Priority Data

Jan. 12, 2005   (JP)   ............... P2005-005039

(51) Int. Cl.
*G06K 9/00* (2006.01)
*A61B 1/06* (2006.01)

(52) U.S. Cl. .................. 382/128; 382/274; 600/160

(58) Field of Classification Search ................ 382/100, 382/128, 129, 130, 131, 132, 133, 134, 162, 382/168, 181, 190, 199, 224, 232, 254, 274, 382/276, 282, 286, 305, 321; 348/70, 65; 600/476, 109, 424, 160; 378/6
See application file for complete search history.

(56) References Cited

U.S. PATENT DOCUMENTS

| | | | |
|---|---|---|---|
| 4,953,539 A * | 9/1990 | Nakamura et al. | 600/109 |
| 5,032,913 A * | 7/1991 | Hattori et al. | 348/70 |
| 6,246,898 B1 * | 6/2001 | Vesely et al. | 600/424 |
| 6,602,186 B1 | 8/2003 | Sugimoto et al. | |
| 6,930,706 B2 * | 8/2005 | Kobayashi et al. | 348/65 |
| 7,235,045 B2 * | 6/2007 | Wang et al. | 600/109 |
| 7,324,674 B2 * | 1/2008 | Ozawa et al. | 382/128 |

(Continued)

FOREIGN PATENT DOCUMENTS

JP   2002-95635   4/2002

(Continued)

OTHER PUBLICATIONS

English language abstract of JP 2002-95635.

(Continued)

*Primary Examiner*—Seyed Azarian
(74) *Attorney, Agent, or Firm*—Greenblum & Bernstein, P.L.C.

(57) ABSTRACT

An image data processor comprising an image signal receiver, a first processing unit, and a second processing unit, is provided. The image signal receiver receives a reference image signal and a laser image signal. The reference image and the laser image correspond to an optical image of an object respectively illuminated by a reference light and a laser light. An average wavelength of the laser light is shorter than that of the reference light. The first processing unit generates reference edge data and a laser edge data based on the reference image signal and the laser image signal respectively. The reference edge data and the laser edge data corresponds to a reference edge image and a laser edge image respectively. The reference edge image and the laser edge image show only edges in the reference image and the laser image respectively. The second processing unit detects a first partial edge based on the reference edge data and the laser edge data. The first partial edge is shown only in one of the reference edge image and the laser edge image.

19 Claims, 12 Drawing Sheets

U.S. PATENT DOCUMENTS

| | | | |
|---|---|---|---|
| 7,328,060 B2 * | 2/2008 | Mooradian et al. | 600/476 |
| 2003/0071894 A1 | 4/2003 | Higuchi et al. | |
| 2003/0176768 A1 | 9/2003 | Gono et al. | |
| 2005/0288553 A1 | 12/2005 | Sugimoto | |
| 2005/0288556 A1 * | 12/2005 | Sugimoto | 600/160 |
| 2006/0020169 A1 | 1/2006 | Sugimoto | |

FOREIGN PATENT DOCUMENTS

JP    2003-93338    4/2003

OTHER PUBLICATIONS

English language abstract of JP 2003-93338.

* cited by examiner

CAPILLARY

CAPILLARY

IMAGE DATA PROCESSOR, COMPUTER PROGRAM PRODUCT, AND ELECTRONIC ENDOSCOPE SYSTEM

BACKGROUND OF THE INVENTION

1. Field of the Invention

The present invention relates to an image signal processor and an electronic endoscope system which carries out an effective image process on image signals so that blood vessels included in an image photographed by an electronic endoscope, are clearly displayed.

2. Description of the Related Art

An electronic endoscope system, used for observing internal organs and making a diagnosis, is well known. The electronic endoscope system illuminates the internal organs, captures an image of the illuminated internal organ, and displays the captured image on a monitor. Capillaries exist at a shallow depth under an inner wall of an organ. Being able to observe capillaries contributes greatly to making a good diagnosis and identifying cancer in an organ. However, it has been difficult to clearly observe capillaries because the inner wall is reddish as are the capillaries, and the capillaries are minute.

Therefore, an electronic endoscope system, that clearly displays blood vessels, is proposed. The endoscope system extracts an area displaying the blood vessels from a whole image based on image signals generated by an imaging device. The endoscope system increases the contrast of the extracted area to a level higher than that of the other areas in the whole image. And then the blood vessel can be clearly displayed. However, it is difficult to extract an area having many blood vessels in the case where the internal organ is illuminated by usual white light. This is because the strength of reflected light at minute capillaries is less than that at other areas.

The relative strength of reflected light at capillaries can be increased by lighting up an inner wall with light having a short wavelength. However, the light having a short wavelength increases not only the relative strength of reflected light at a capillary, but also the relative strength at another organ and another blood vessel that exist in a littler deeper depth than the capillaries. Accordingly, it is difficult to instantly observe only capillaries.

SUMMARY OF THE INVENTION

Therefore, an object of the present invention is to provide an image data processor and an electronic endoscope system that can process image signals so that only capillaries appear in an image corresponding to the image signal is displayed.

According to the present invention, an image data processor comprising an image signal receiver, a first processing unit, and a second processing unit, is provided. The image signal receiver receives a reference image signal and a laser image signal generated by an imaging device. The reference image signal is generated by the imaging device when the imaging device captures a reference image. The reference image is an optical image of an object illuminated by a reference light. The laser image signal is generated by the imaging device when the imaging device captures a laser image. The laser image is an optical image of an object illuminated by a laser light. An average wavelength of the laser light is shorter than that of the reference light. The first processing unit generates reference edge data and a laser edge data based on the reference image signal and the laser image signal respectively. The reference edge data corresponds to a reference edge image. The reference edge image shows only edges. The laser edge data corresponds to a laser edge image. The laser edge image shows only edges. The second processing unit detects a first partial edge based on the reference edge data and the laser edge data. The first partial edge is shown only in one of the reference edge image and the laser edge image.

Further the second processing unit generates first partial edge data. The first partial edge data corresponds to a first partial edge image. The first partial edge image shows the first partial edge.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
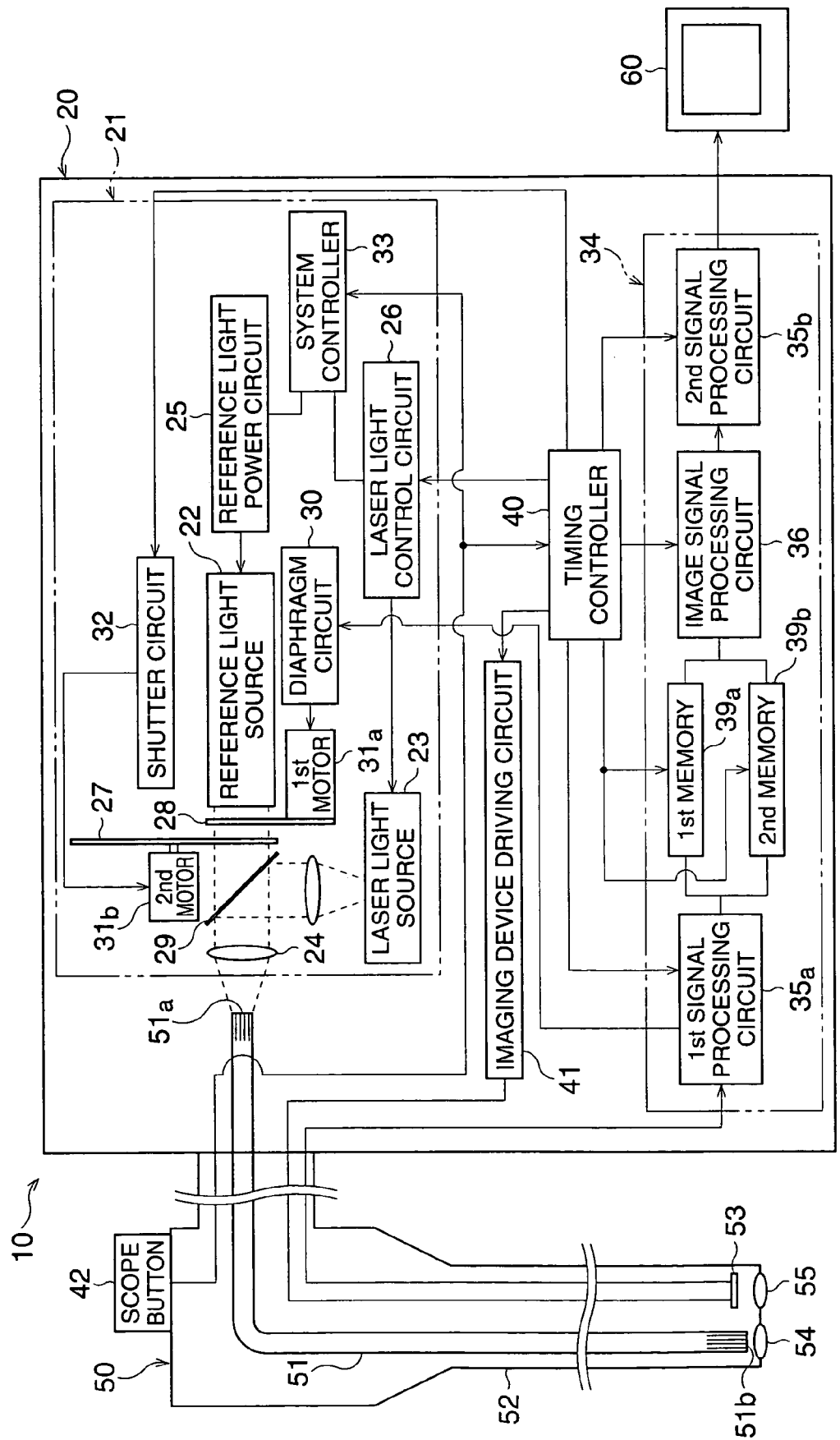
FIG. 1 is a block diagram showing the internal structure of an electronic endoscope system having an image data processor of an embodiment of the present invention.

The present invention is described below with reference to the embodiment shown in the drawings.

In the FIG. 1, an electronic endoscope system 10 comprises an endoscope processor 20, an endoscope 50, and a monitor 60. The endoscope processor 20 is connected to the endoscope 50 and the monitor 60.

A light system 21 is housed in the endoscope processor 20. The light system 21 emits light to illuminate a required object. The light, that the light system emits, is transmitted by the light guide 51 housed in the endoscope 50. And the required object is illuminated by the transmitted light.

The endoscope 50 comprises an imaging device 53, such as CCD, at the head end of an insert tube 52. The imaging device 53 receives an optical image of the required object. The imaging device 53 generates image signals corresponding to the received image. The image signal is sent to the endoscope processor 20. The endoscope processor 20 comprises an image process system 34. The image process system 34 carries out some predetermined signal processes for the image signals. The endoscope processor 20 can generate partial edge data, described in detail later. The predetermined signal processes include not only the partial-edge process but also the usual signal processes, such as a gamma process, white balance process, and so on. The image signal, having had the predetermined processes carried out, is sent to the monitor 60.

An image corresponding to the image signal sent to the monitor 60, is displayed on the monitor 60.

The light system 21 comprises a reference light source 22, a laser light source 23, condenser lens 24, a reference light power circuit 25, a laser light control circuit 26, shutter 27, diaphragm 28, and so on.

A reference light source 22 emits reference light, such as white light. A laser light source 23 emits laser light, such as ultraviolet light, having an average wavelength that is shorter than the wavelength of the reference light. The diaphragm 28, shutter 27, dichroic mirror 29, and the condenser lens 24 are mounted in an optical path of the reference light emitted by the reference light source 22 to the incident end 51a of the light guide 51. The reference light, which is almost all parallel light beams, is made incident on the incident end 51a, through the dichroic mirror 29 and the condenser lens 24. The condenser lens 24 condenses the reference light for the incident end 51a.

A reference light intensity is adjusted by driving the diaphragm 28. A first motor 31a, controlled by the diaphragm circuit 30, drives the diaphragm 28. The diaphragm circuit 30 is connected to a first signal processing circuit 35a. The first signal processing circuit 35a detects the amount of light received for a received image based on the image signals generated by the imaging device 53. The diaphragm circuit 30 calculates a driving quantity of the first motor 31a based on the amount of light received.

Figure 2:
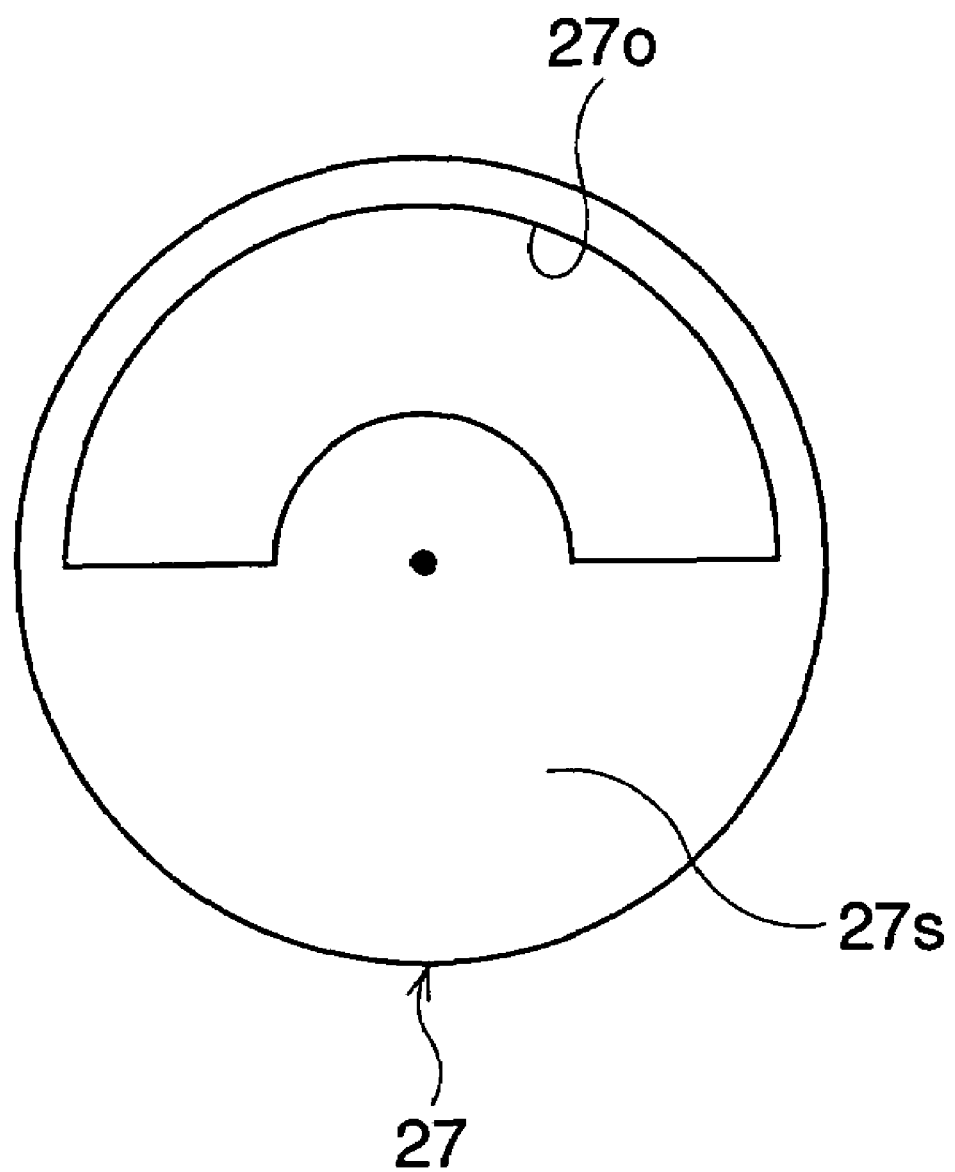
FIG. 2 is a plan of the shutter.

The shutter 27 is a rotary shaped shutter as shown in FIG. 2. Passing through or shielding the reference light is changed by driving the shutter 27. The shutter 27 has an aperture 27o and a shielding plate 27s. The aperture 27o is inserted into the optical path of the reference light when the reference light is controlled to pass through the optical path. The shielding plate 27s is inserted into the optical path of the reference light when the reference light is shielded. A second motor 31b, controlled by a shutter circuit 32, drives the shutter 27.

The laser light beams emitted by the laser light source 23 are almost all parallel. The laser light source 23 is mounted so that the laser light beams, that are almost all parallel, are incident on the incident end 51a after being reflected by the dichroic mirror 29. For example, when a laser light source 23 is set up so that an angle between the optical paths of the reference light and the laser light is 90 degrees, the dichroic mirror 29 is mounted at an angle of 45 degrees between a plane of the dichroic mirror 29 and the optical path of the reference light. The laser light control circuit 26 controls the switching of the laser light source 23 on and off.

The shutter circuit 32 and the laser light control circuit 26 are connected to a timing controller 40. The timing controller 40 outputs a shutter timing signal to the shutter circuit 32. The shutter timing signal controls an amount of time the reference light passes through the shutter 27, and an amount of time the reference light is shielded. Further, the timing controller 40 outputs an emission timing signal to the laser light control circuit 26. The emission timing signal controls a timing to switch the laser light source 23 on and off.

The timing controller 40 outputs the shutter timing signal and the emission timing signal so that the laser light source 23 is switched off when the reference light is controlled to pass through the shutter 27. The timing controller 40 outputs the shutter timing signal and the emission timing signal so that the laser light source 23 is switched on when the reference light is shielded by the shutter 27. Accordingly, switching light to illuminate the required object is carried out by cooperation of the timing controller 40, the laser light control circuit 26, the shutter circuit 32, the second motor 31b, and the shutter 27.

Further, the timing controller 40 outputs a necessary timing signal for driving the imaging device 53, to an imaging device driving circuit 41. Further still, the timing controller 40 is connected to the image process system 34, and the timing controller 40 outputs another timing signal, described later, to the image process system 34.

Power for the reference light source 22 is supplied by the reference light power circuit 25. The reference light power circuit 25 and the laser light control circuit 26 are connected to a system controller 33. The reference light power circuit 25 and the laser light control circuit 26 are started by switching on scope button 42, which is connected to the system controller 33.

As described above, the reference light or the laser light is incident on the incident end 51a of the light guide 51. The light transmitted to the out end 51b of the light guide 51 illuminates a peripheral area nearby the head end of the insert tube 52 through a diffuser lens 54. An optical image of the required object is received by the imaging device 53 through an object lens 55. The imaging device 53 is controlled by the imaging device driving circuit 41 so that the imaging device 53 receives the optical image of one frame at least while the required object is continuously illuminated by the reference light. Or the imaging device 53 is controlled by the imaging device driving circuit 41 so that the imaging device 53 receives the optical image of one frame at least while the required object is illuminated by the laser light.

The image process system 34 comprises the first signal processing circuit 35a, a second signal processing circuit 35b, an image signal processing circuit 36, and first and second memories 39a, 39b.

The imaging device 53 is connected to the first signal processing circuit 35a. An image signal generated by the imaging device 53 is received by the first signal processing circuit 35a. The first signal processing circuit 35a carries out the predetermined signal processes, for example white balance process, gamma correction process, and so on for the image signal. In addition, the analog image signal is converted to a digital image data.

The first signal processing circuit 35a is connected to the timing controller 40. The timing controller 40 repeatedly and reciprocally outputs a reference timing signal and a laser timing signal. The reference timing signal is output at the same time the reference light is controlled to pass through the shutter 27. The laser timing signal is output at the same time the laser light source 23 is switched on.

The first signal processing circuit 35a recognizes the image signal, generated while receiving the reference timing signal, as a reference image signal. The reference image signal corresponds to a reference image that is captured while the required object is illuminated by the reference light (reference to FIG. 3). On the other hand, the first signal processing circuit 35a recognizes the image signal, generated while receiving the laser timing signal, as a laser image signal. The laser image signal corresponds to a laser image that is captured while the required object is illuminated by the laser light (reference to FIG. 4).

Figure 5:
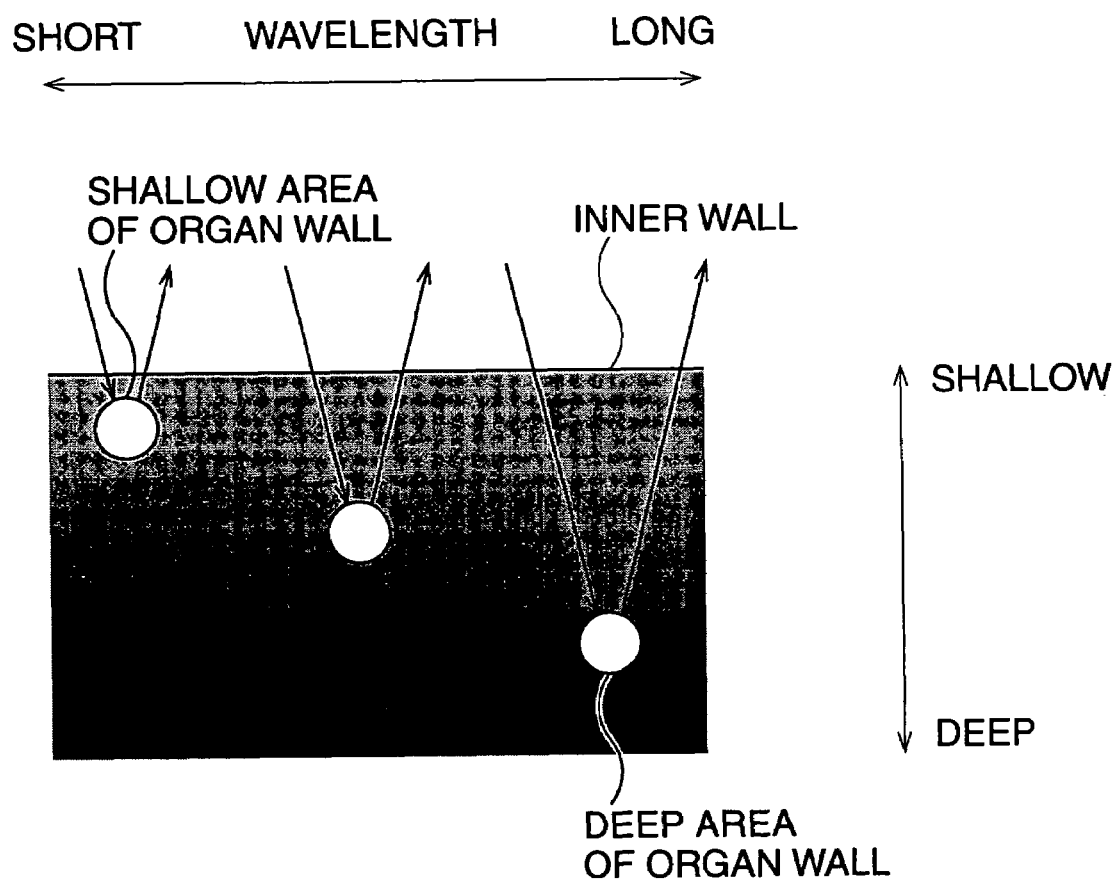
FIG. 5 is a diagram showing that a depth which a light reaches varies according to a wavelength of the light.

If the wavelength of light for illuminating an organ is short, the light reaches a shallow depth under an inner wall of the organ, as shown in FIG. 5. Accordingly, the reflected light strength from an area located at a shallow depth under the inner wall of an organ is relatively large. On the other hand, as the wavelength of the light for illuminating an area of an organ gets longer, the light reaches deep depth under the inner wall of the organ. Accordingly, the reflected light strength of an area of an organ located at a deep depth under the inner wall is relatively large.

Figure 4:
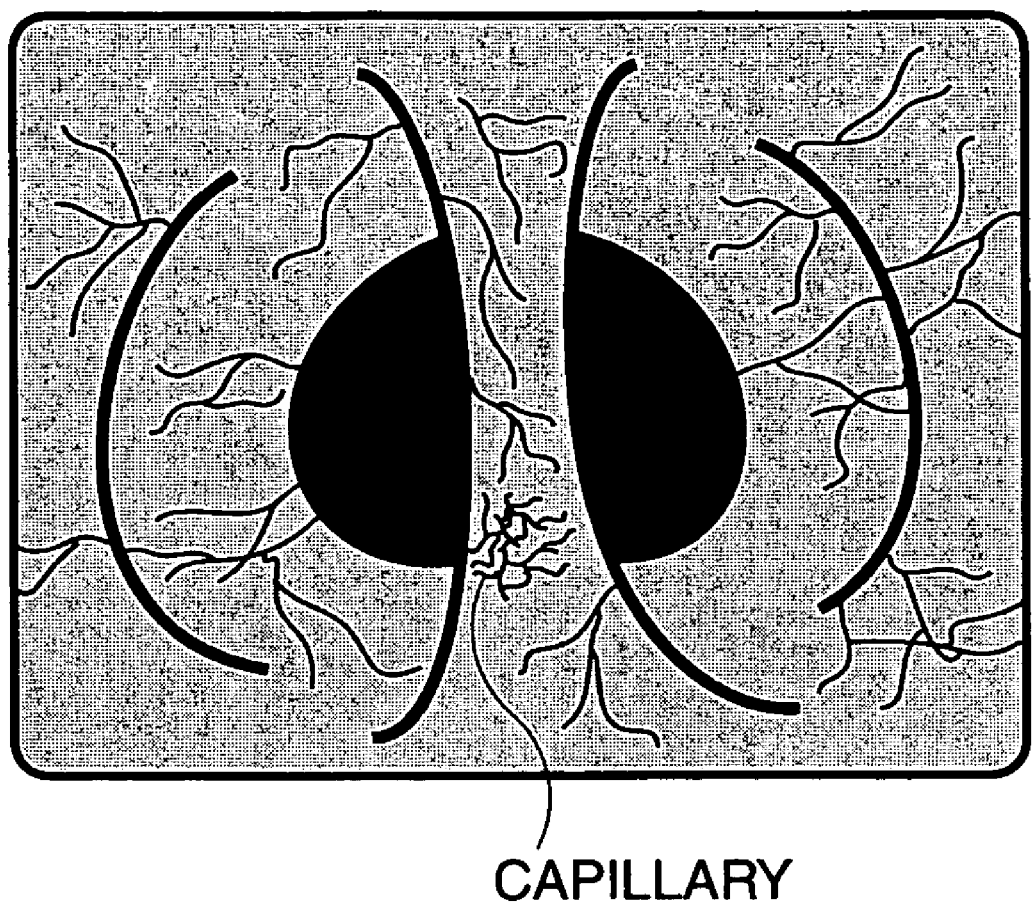
FIG. 4 illustrates a laser image.

Capillaries, that generally exist at a shallow depth under an inner wall, are displayed more clearly in the laser image, as shown in FIG. 4. This is because the laser image is received by the imaging device while the inner wall is illuminated with the laser light having a short wavelength.

Figure 3:
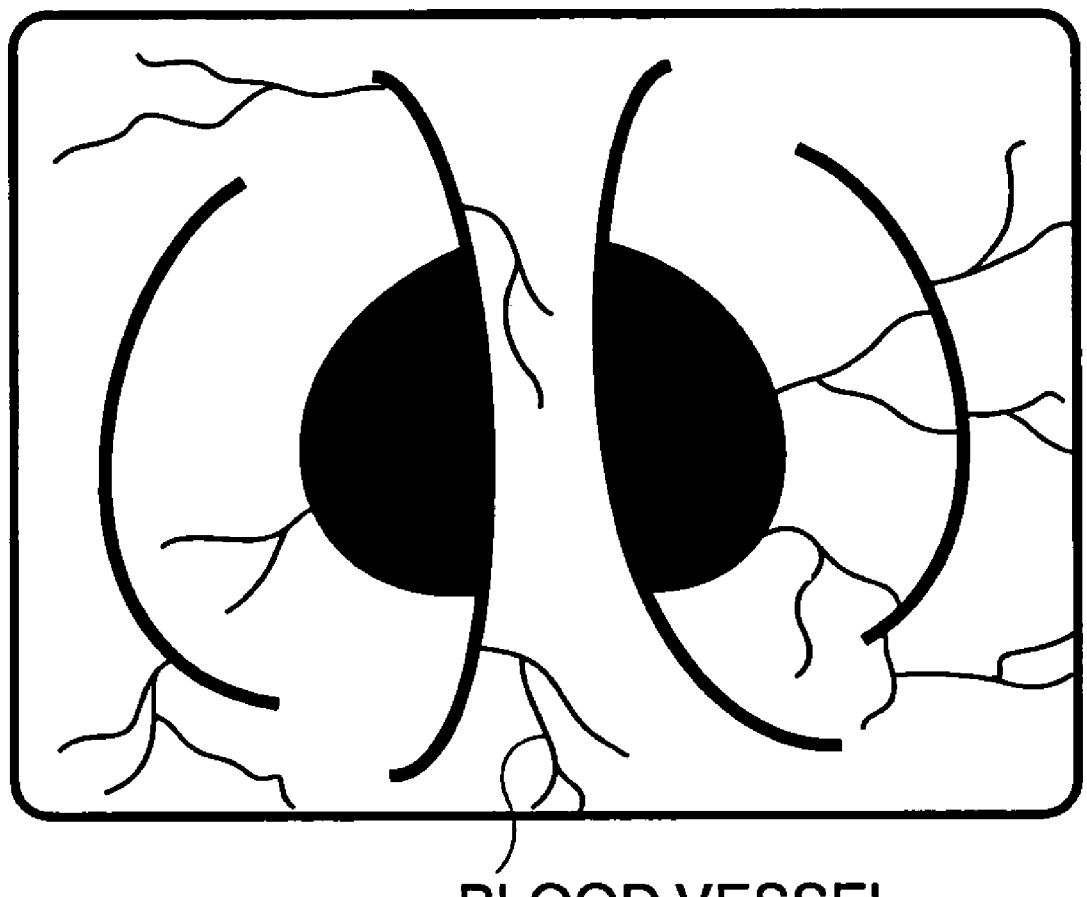
FIG. 3 illustrates a reference image.

On the other hand, blood vessels, that generally exist at a deeper depth under the inner wall, are displayed in the reference image, as shown in FIG. 3. Because the reference image is received by the imaging device while the inner wall is illuminated with the reference light having a wider range of wavelengths of light. The capillaries that are located at a shallow depth are not practically well displayed while using the reference image, because the amount of light reflected by an area of an organ located at a shallow depth is less than that at a deeper depth.

The first signal processing circuit 35a is connected to the first and second memories 39a and 39b. The reference image data, corresponding to the reference image signal, is stored in the first memory 39a. The laser image data, corresponding to the laser image signal, is stored in the second memory 39b. The first and second memories 39a and 39b are connected to the timing controller 40. The timing controller 40 controls the timing for storing the reference image data and the laser image data respectively in the first and second memories 39a and 39b.

The first and the second memories 39a and 39b are connected to the image signal processing circuit 36. The image signal processing circuit 36 carries out a normalization process, an edge-extraction process, and a partial edge data process for the reference image data and the laser image data.

The normalization process is carried out by the following four steps. In the first step, a reference luminance, that is an average luminance of the whole reference image, is calculated based on the reference image data. In the second step, laser luminance, that is an average luminance of the whole laser image, is also calculated based on the laser image data. In the third step, a normalizing-ratio of the reference luminance to the laser luminance is calculated. In the fourth step, normalized laser image data is generated by multiplying the luminance of each pixel forming the laser image by the calculated normalizing-ratio. The normalized laser image data is formed from one frame of normalized pixel data corresponding to the normalized luminance of each pixel.

Figure 6:
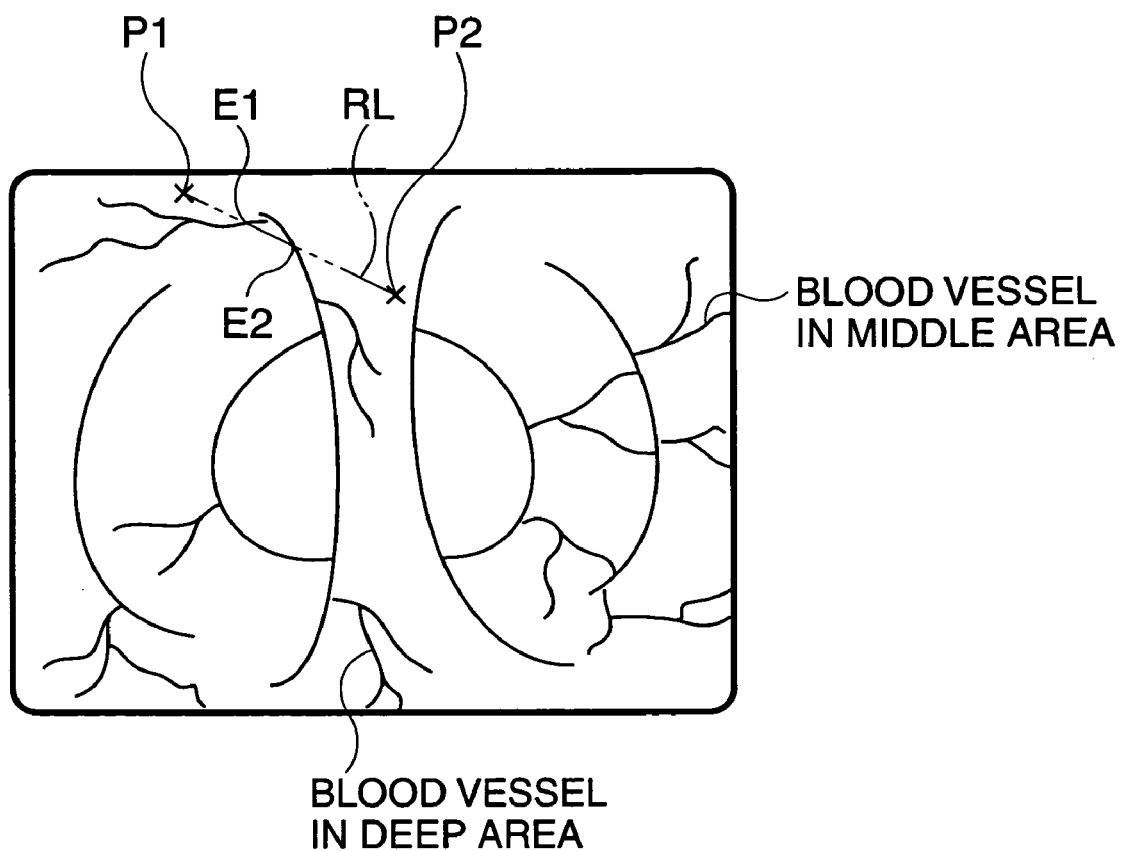
FIG. 6 illustrates a reference edge image.
Figure 7:
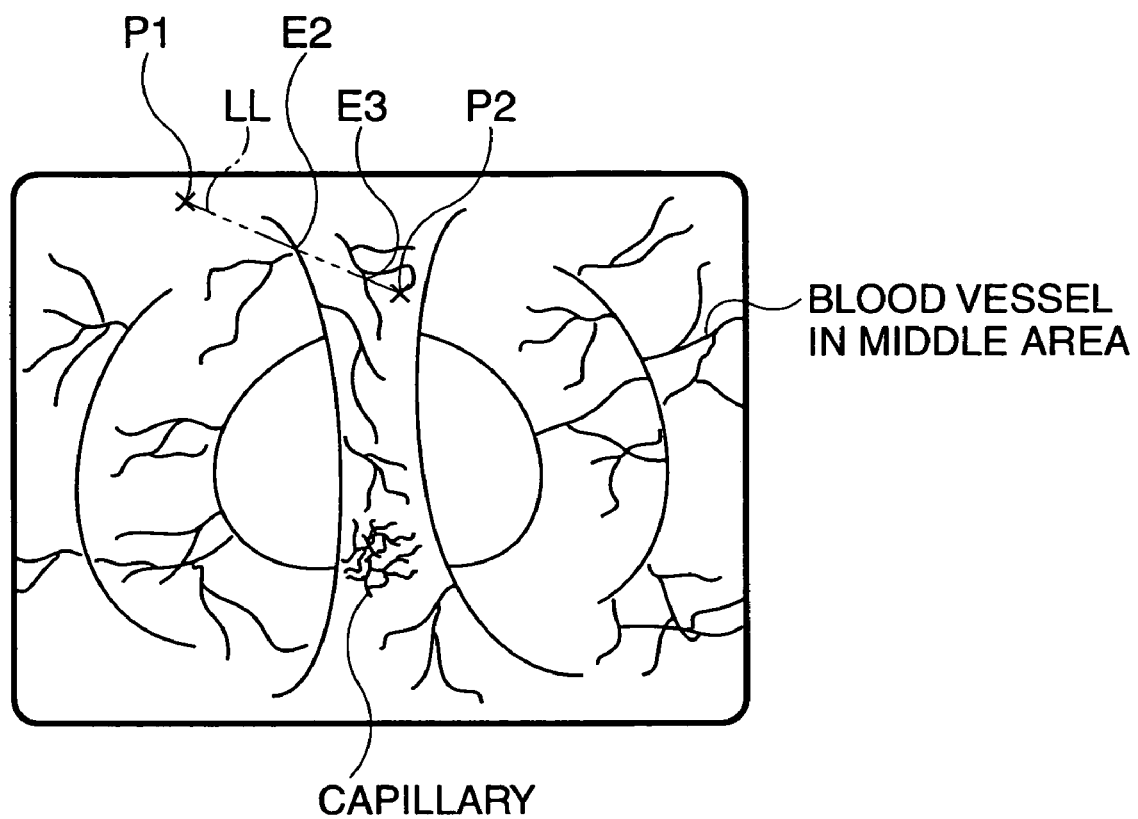
FIG. 7 illustrates a laser edge image.

The edge-extraction process is carried out after the normalization process. In the edge-extraction process, an edge is extracted from the entire reference image or the entire normalized laser image corresponding to the normalized laser image data. More specifically, a pixel displaying an edge is detected from all pixels forming the reference image and the normalized laser image by any known means for detecting an edge from an image, for example a difference operator. And then the image data, corresponding to an image formed by the pixels displaying an edge, is generated. Reference edge data and laser edge data is generated by carrying out the edge-extraction process respectively for the reference image data and the normalized laser image data. The reference edge data corresponds to a reference edge image as shown in FIG. 6. The laser edge data corresponds to a laser edge image as shown in FIG. 7.

Figure 8:
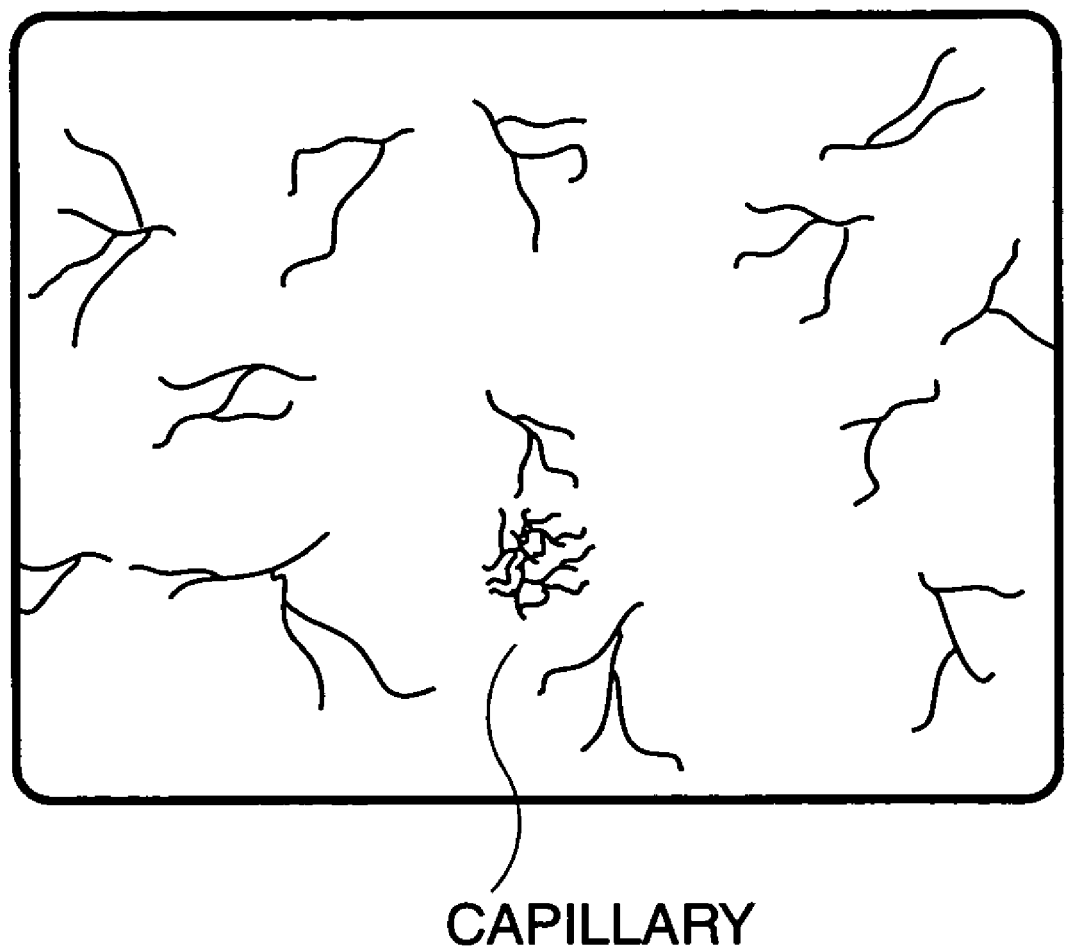
FIG. 8 illustrates a partial edge image.

The partial edge data process is carried out after the edge-extraction process. Partial edge data corresponding to a partial edge image is generated by the partial edge data process based on the reference edge data and the laser edge data. An edge, that is not displayed in the reference edge image but is in the laser edge image, is displayed in the partial edge image as shown in FIG. 8. For example, a blood vessel at a deep depth under an inner wall is displayed in the reference edge image as shown in FIG. 6. But the blood vessel at a deep depth is not displayed in the laser edge image and the partial edge image as shown in FIGS. 7 and 8. A blood vessel at a middle depth under an inner wall is displayed in the reference edge image and the laser edge image. But the blood vessel at the middle depth is not displayed in the partial edge image. A capillary at a shallow depth under an inner wall is not displayed in the reference edge image but is displayed in the laser edge image. The capillary is displayed in the partial edge image.

Figure 9A:
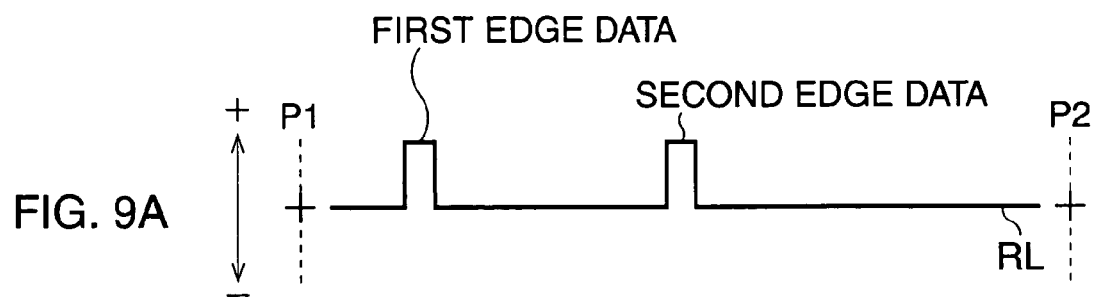
FIG. 9A shows luminance along a line connecting first and second points in FIG. 6.
Figure 9B:
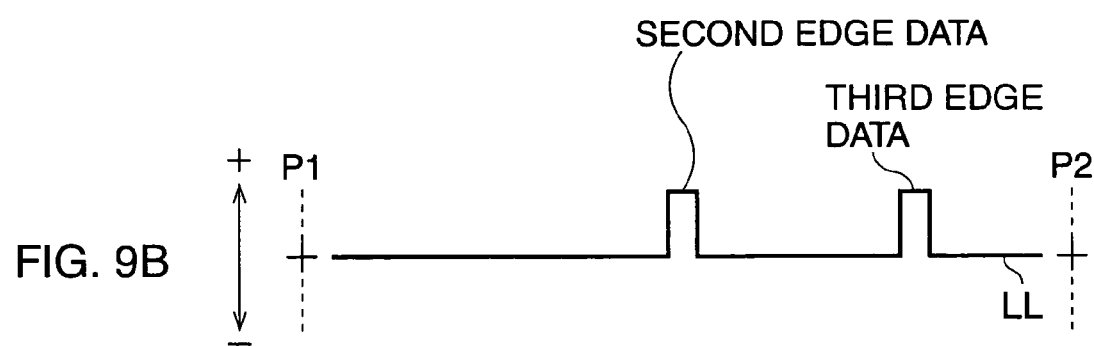
FIG. 9B shows luminance along a line connecting first and second points in FIG. 7.
Figure 9C:
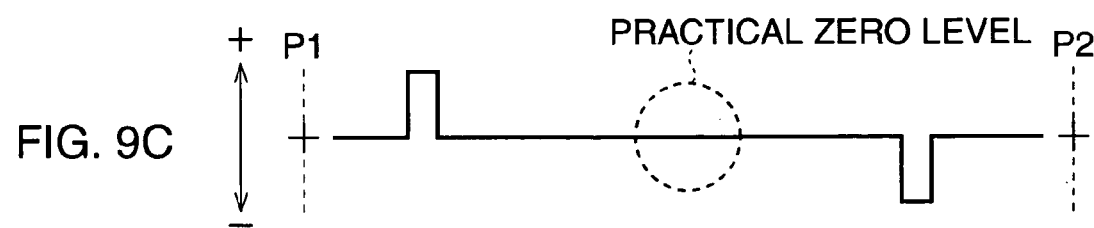
FIG. 9C shows a difference of luminance in FIGS. 6 and 7.

It is explained below, how to generate the partial edge data based on the reference edge data and the laser edge data with reference to FIGS. 9A, 9B, and 9C. FIG. 9A shows luminance along a line connecting first and second points in FIG. 6. Hereinafter, the first and second points are referred to respectively as P1 and P2. FIG. 9B shows luminance along a line connecting P1 and P2 in FIG. 7. Hereinafter, the line connecting P1 and P2 in FIGS. 6 and 7 are referred to respectively as RL and LL. FIG. 9C shows the difference in luminance between the reference edge image shown in FIG. 6 and the laser edge image shown in FIG. 7 along a line connecting P1 and P2. In FIG. 9A and 9B, an edge is detected when a pixel luminance level is positive.

A first edge, hereinafter referred to as E1, is displayed only in the reference edge image as shown in FIG. 6. A second edge, hereinafter referred to as E2, is displayed both in the reference edge image and the laser edge image. A third edge, hereinafter referred to as E3, is displayed only in the laser edge image. The edges E1 and E2 are detected at pixels where the luminance is positive in the reference edge image as shown in FIG. 9A. The edges E2 and E3 are detected at pixels where the luminance is positive in the laser edge image as shown in FIG. 9B.

It can be judged which pixels display an edge in the laser edge image by using subtracted-luminance levels calculated by subtracting the laser edge data from the reference edge data. An edge displayed only in the reference edge image, for example the edge E1, is detected at a pixel where the subtracted-luminance level is positive, as shown in FIG. 9C. The subtracted-luminance level at a pixel, where an edge displayed both in the reference edge image and the laser edge image for example the edge E2, practically becomes zero, as shown in FIG. 9C. An edge displayed only in the laser edge image, for example the edge E3, is detected at a pixel where the subtracted-luminance level is negative, as shown in FIG. 9C. The partial edge data is generated by extracting a pixel where a subtracted-luminance level is negative.

The image signal processing circuit 36 is connected to the second signal processing circuit 35b. The partial edge data is output to the second signal processing circuit 35b. The partial edge data, which is digital, is converted to analog partial edge signals by the second signal processing circuit 35b. The second signal processing circuit 35b carries out some predetermined signal processes, for example a clamp process and a blanking process, for the partial edge signals after D/A conversion.

The second signal processing circuit 35b is connected to the monitor 60. The second signal processing circuit 35b outputs the partial edge signal to the monitor 60. The partial edge image is displayed over the whole displaying surface on the monitor 60.

The second signal processing circuit 35b is connected also to the first and the second memories 39a and 39b (not depicted in FIG. 1). The second signal processing circuit 35b can receive the reference image data stored in the first memory 39a and the laser image data stored in the second memory 39b. And the second signal processing circuit 35b can convert the reference image data or the laser image data, which are digital, to the reference image signals and the laser image signals respectively, that are analog. Further, the second signal processing circuit 35*b* can carry out the predetermined signal processes for the reference image signal or the laser image signal.

Figure 10:
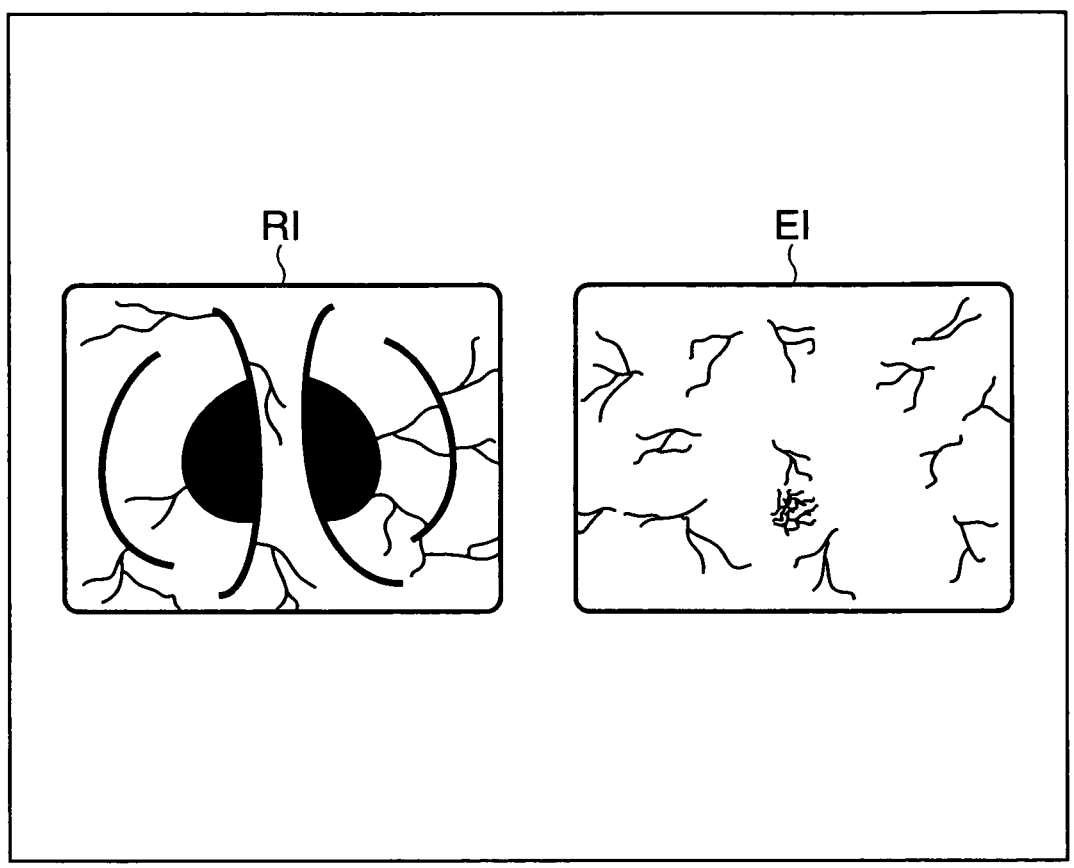
FIG. 10 illustrates a monitor displaying a partial edge image and a reference image.
Figure 11:
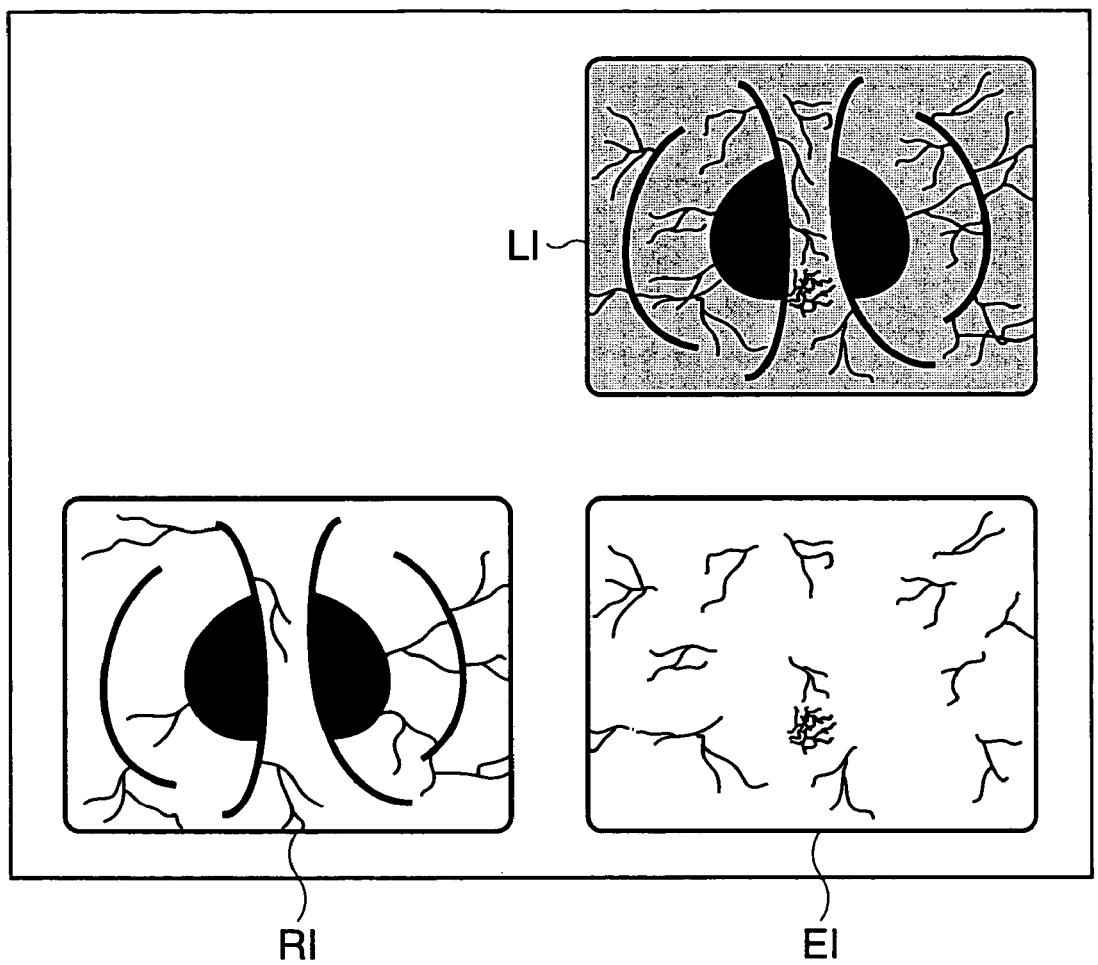
FIG. 11 illustrates a monitor displaying a partial edge image, a reference image, and a laser image.

The image displayed on the monitor 60 can be selected from the partial edge image, the reference image, and the laser image by a user. Or two or all of the images from the partial edge image, the reference image, and the laser image can be displayed as shown in FIGS. 10 and 11. A display change button (not depicted) can be pushed by a user and then an image displayed on the monitor is changed. In FIGS. 10 and 11, the partial edge image, the reference image, and the laser image are respectively referred to as EI, RI, and LI.

In the case where plural images are displayed, the second signal processing circuit 35*b* carries out allocation of area to display each image and scales down each image. The second signal processing circuit 35*b* is connected to the timing controller 40. The allocation of the areas and the scaling down of each image are carried out based on a timing signal output from the timing controller 40.

Figure 12:
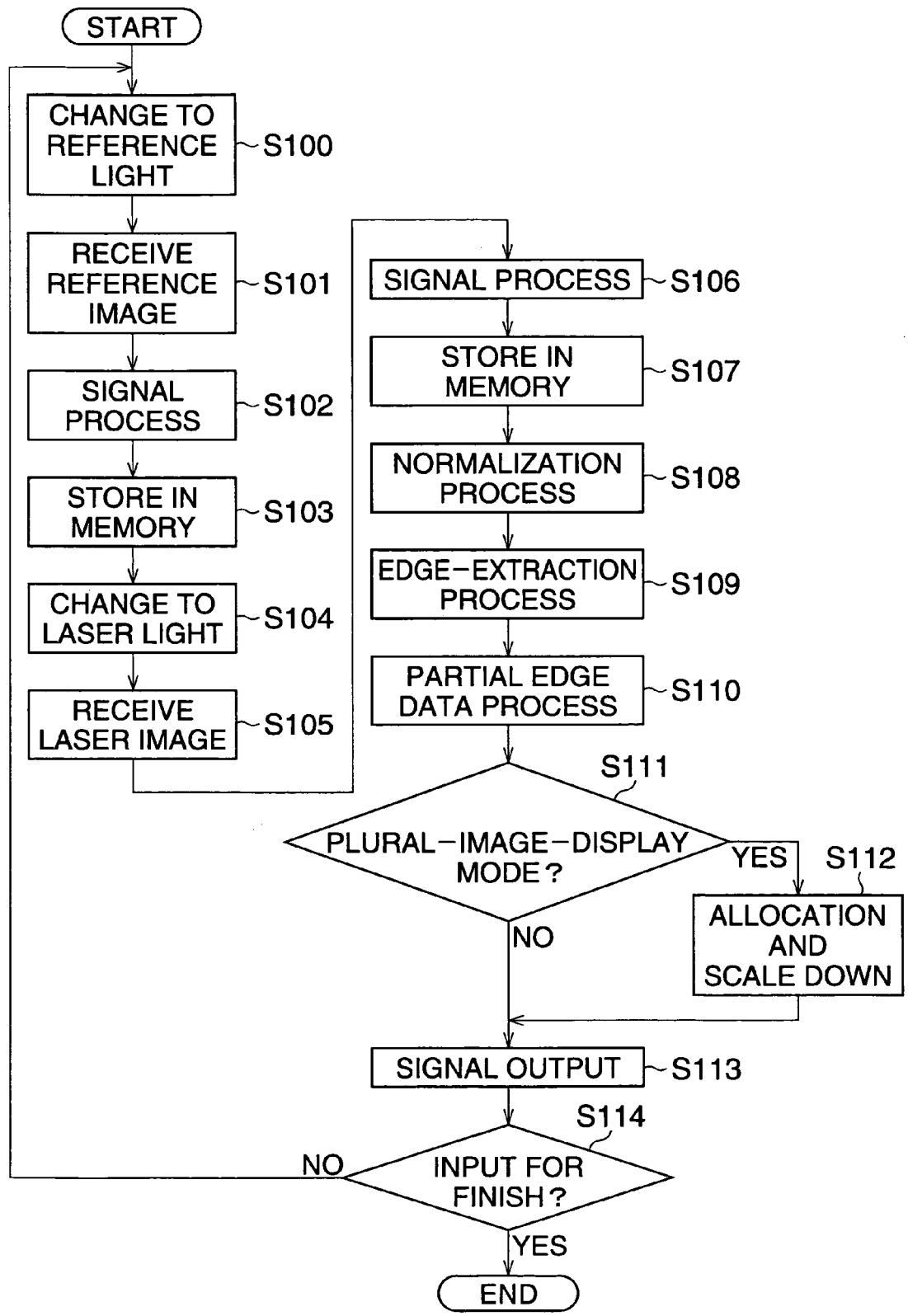
FIG. 12 is a flowchart to explain the control process and the image data process.

Next, control processes and image signal processes carried out by the endoscope processor 20 are explained below using the flowchart of FIG. 12.

The control processes and the image signal processes of this embodiment start when a partial edge image displaying mode is selected to display the partial edge image on the monitor 60. At step S100, the shutter timing signal is output to the shutter circuit 32 so that the shutter is driven to insert the aperture 27*o* into the optical path of the reference light. Then the light to illuminate a required object is changed to the reference light by driving the shutter 27.

At step S101, the imaging device 53 is driven to receive the optical image of the required object that is illuminated by the reference light. And then the process goes to step S102. At step S102, the predetermined signal processes, including the A/D conversion process, are carried out for the reference image signal generated by the imaging device 53. The reference image signal, which is analog, is converted to digital reference image data by the predetermined processes.

At step S103, the reference image data is stored in the first memory 39*a*, and then the process goes to step S104. At step S104, the emission timing signal for emitting the laser light is output to the laser light control circuit 26.

At step S105, the imaging device 53 is driven to receive the optical image of the required object that is illuminated by the laser light. The predetermined signal processes, including the A/D conversion process, are carried out for the laser image signal generated by the imaging device 53. Then the analog laser image signal, is converted to laser image data by predetermined processes at step S106.

At step S107, the laser image data is stored in the second memory 39*b*. At next step S108, the normalization process is carried out for the laser image data based on the reference luminance and the laser luminance. Then the normalized laser image data is generated.

After generating the normalized laser image data, the process goes to step S109. At step S109, the edge-extraction process is carried out for the reference image data and the normalized laser image data. Then the reference edge data and the laser edge data are generated.

At the next step S110, the partial edge data is generated based on the reference edge data and the laser edge data, then the processes goes to step S111. At step S111, it is judged whether a plural-image-display mode, where the partial edge image is displayed with at least one of the reference image and the laser image, is selected or not. The process goes to step S112 when the plural-image-display mode is selected. At step S112, allocation of areas to display each image, and the scaling down of each image are carried out.

The process goes to step S113 when the plural-image-display mode is not selected at step S111 or when the process of step S112 finishes. At step S113, the partial edge signal or a complex image signal corresponding to plural images including the partial edge image is output to the monitor 60.

At the next step S114, it is judged whether the partial edge image displaying mode has finished due to changing the displayed image to another image. When the partial edge image displaying mode is finished, the control processes and the image signal processes are completed. On the other hand, the process returns to step S100 when there is no input to finish. The processes from step S100 to step S114 are repeated until there is an input to finish.

In the above embodiment, an area of an organ at a shallow depth under an inner wall, for example a capillary, can be displayed in a partial edge image clearly and in detail. Accordingly, a user can detect features, such as cancers, more easily.

Further in the above embodiment, one of the reference image and the laser image at least is displayed with the partial edge image on the monitor 60 in the plural-image-display mode. A user, that is a doctor, usually will want to see the reference image or the laser image when he observes the partial edge image. Accordingly, he can see the reference image and/or the laser image with the partial edge image without changing the image displayed on the monitor 60. Consequently, the time for medical examination can be reduced.

The partial edge data is generated by extracting a pixel where a subtracted-luminance level is negative in the above embodiment. However, it is possible to generate the partial edge data by extracting a pixel where an absolute subtracted-luminance level is above a predetermined threshold level. In such a case, an edge displayed only in the laser edge image can be extracted even though a luminance level of the same edge in the reference edge data and the laser edge data is not completely according each other.

The partial edge data is generated after subtracting the laser edge data from the reference edge data in the above embodiment. However, it is possible to generate the partial edge data after subtracting the reference edge data from the laser edge data. The partial edge data should be generated by extracting a pixel where a subtracted luminance level is positive in the case of subtracting the reference edge data from the laser edge data.

Only capillaries and so on that exist at a shallow depth under an inner wall of an organ are displayed, in the above embodiment. However, it is possible to display only blood vessels and so on that exist at a deeper depth. Such a partial edge image showing only the blood vessels and so on is displayed by extracting pixels where a subtracted-luminance level is positive. Or it is possible to extract pixels showing blood vessels and so on that exist at a desired depth under the inner wall and to display a partial edge image showing only the blood vessels and so on that exist at the desired depth by selecting the reference light source and the laser light source that respectively emit reference light of an adequate wavelength and laser light of an adequate wavelength.

Only an edge at a pixel where a subtracted-luminance level is negative, is extracted and displayed in the partial edge image, in the above embodiment. However, it is possible to detect an edge at a pixel where a subtracted-luminance level is negative and to display an entire image where a first hue of the pixel, for example red, is emphasized. Or it is possible to detect an edge at a pixel where a subtracted-luminance level is positive and to display an entire image where a second hue of the pixel, for example blue, is emphasized. Or it is possible to detect an edge at a pixel where a subtracted-luminance level is not zero, and to display an entire image where the first hue of the pixel, where a subtracted-luminance is negative, and the second hue of the pixel, where a subtracted-luminance is positive, are emphasized. It is possible for an operator to identify a location of a capillary with such a transformation. This contributes to the accurate diagnosis.

The normalized laser image data is generated by multiplying the luminance of each pixel used to form the laser image by the calculated normalizing-ratio, in the above embodiment. However, it is possible to generate the normalized reference image data by multiplying the luminance of each pixel used to form the reference image by a reciprocal number of the normalizing-ratio. In this case, the reference edge data and the laser edge data are generated by carrying out the edge-extraction process respectively for the normalized reference image data and the laser image data.

A pixel showing an edge in the laser image only is detected by subtracting the laser edge data from the reference edge data, in the above embodiment. However, any other means for detecting such a pixel showing an edge in the laser image only may be applicable. For example, it is possible to generate the partial edge data by carrying out an exclusion process that excludes a pixel showing an edge in the reference image from a pixel showing an edge in the laser image.

The normalization process is carried out before the edge-extraction process, in the above embodiment. However the normalization process is not necessary as long as the edge-extraction process is carried out for pixels excluding the pixel showing an edge both in the reference image and the laser image. The normalization process is not necessary if the exclusion process mentioned above is present.

The above embodiment can be implemented by installing a program for generating partial edge data into an all purpose image data processor, which can be connected to the reference and laser light sources.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2005-005039 (filed on Jan. 12, 2005), which is expressly incorporated herein, by reference, in its entirety.

The invention claimed is:

1. An image data processor, comprising:
   an image signal receiver that receives a reference image signal, generated by an imaging device when said imaging device captures a reference image that is an optical image of an object illuminated by a reference light, and a laser image signal, generated by said imaging device when said imaging device captures a laser image that is an optical image of said object illuminated by a laser light, said laser light having a shorter average wavelength than that of said reference light;
   a first processing unit that generates reference edge data, corresponding to a reference edge image showing only edges, based on said reference image signal, and a laser edge data, corresponding to a laser edge image showing only edges, based on said laser image signal; and
   a second processing unit that detects a first partial edge shown only in one of said reference edge image and said laser edge image, based on said reference edge data and said laser edge data;
   wherein said second processing unit generates second partial edge data corresponding to a second partial edge image showing said reference image or said laser image, while emphasizing a first hue of said first partial edge.

2. An image data processor according to claim 1, wherein said second processing unit generates first partial edge data corresponding to a first partial edge image showing said first partial edge.

3. An image data processor according to claim 2, further comprising;
   a signal feeder that outputs a video signal, corresponding to an image including said reference image and said first partial edge image, to a monitor for displaying an optical image received by said imaging device.

4. An image data processor according to claim 1, wherein said second processing unit detects a second partial edge only in another of said reference edge image and said laser edge image, and said second processing unit generates said second partial edge data corresponding to said second partial edge image while further emphasizing a second hue of said second partial edge.

5. An image data processor according to claim 1, further comprising;
   a third processing unit that generates normalized laser image data, by normalizing the luminance of said laser image with the luminance of said reference image, or normalized reference image data, by normalizing luminance of said reference image with the luminance of said laser image;
   wherein said first processing unit generates said reference edge data and said laser edge data based on one of, said reference image signal and said normalized laser image data, and, said laser image signal and said normalized reference image data, and said second processing unit detects said first partial edge based on a difference of luminance in each pixel forming said reference edge image and said laser edge image.

6. An image data processor according to claim 5, wherein said third processing unit carries out a normalization process by making an average luminance of said laser image agree with an average luminance of said reference image, or the average luminance of said reference image agree with the average luminance of said laser image.

7. An image data processor according to claim 5, wherein said second processing unit detects said first partial edge by extracting only a pixel where said difference of luminance is one of a positive difference and a negative difference.

8. An image data processor according to claim 7, wherein said second processing unit detects a second partial edge, only in the other of said reference edge image and said laser edge image, by extracting a pixel where difference of luminance is the other of the positive difference and a negative difference.

9. An image data processor according to claim 5, wherein said second processing unit detects said first partial edge by extracting a pixel where the absolute difference of luminance in said reference edge image and said laser edge image is above a predetermined threshold value.

10. An image data processor according to claim 1, further comprising:

a controller that makes one of said reference light and said laser light illuminate said required object; and a fourth processing unit that recognizes an image signal, generated while said controller controls said reference light to illuminate said object, as said reference image signal; and another image signal, generated while said controller controls said laser light to illuminate said required object, as said laser image signal.

11. A computer that stores and executes a computer program, the computer comprising:

an image signal receiver that receives a reference image signal generated by an imaging device when said imaging device captures a reference image that is an optical image of an object illuminated by a reference light, and a laser image signal generated by said imaging device when said imaging device captures a laser image that is an optical image of said object illuminated by a laser light said laser light having a shorter average wavelength than that of said reference light;

a generating processor that generates reference edge data corresponding to a reference edge image showing only edges, based on said reference image signal, and laser edge data corresponding to a laser edge image showing only edges, based on said laser image signal;

and a detecting processor that detects a first partial edge only in one of said reference edge image and said laser edge image based on said reference edge data and said laser edge data;

wherein said detecting processor generates second partial edge data corresponding to a second partial edge image showing said reference image or said laser image, while emphasizing a first hue of said first partial edge.

12. An electronic endoscope system, comprising:

an electronic endoscope having an imaging device that generates a reference image signal when said imaging device captures an optical image of a required object illuminated by a reference light, and a laser image signal when said imaging device captures an optical image of said required object illuminated by a laser light, said laser light having a shorter average wavelength than that of said reference light;

a first processing unit that generates reference edge data corresponding to a reference edge image showing only edges, based on said reference image signal, and laser edge data corresponding to a laser edge image showing only edges, based on said laser image signal;

a second processing unit that detects a first partial edge only in one of said reference edge image and said laser edge image, based on said reference edge data and said laser edge data, and generates first partial edge data corresponding to a first partial edge image showing said first partial edge; and a monitor that displays said first partial edge image;

wherein said second processing unit generates second partial edge data corresponding to a second partial edge image showing said reference image or said laser image, while emphasizing a first hue of said first partial edge.

13. An image data processor, comprising:

an image signal receiver that receives a reference image signal, generated by an imaging device when said imaging device captures a reference image that is an optical image of an object illuminated by a reference light, and a laser image signal, generated by said imaging device when said imaging device captures a laser image that is an optical image of said object illuminated by a laser light, said laser light having a shorter average wavelength than that of said reference light;

a first processing unit that generates reference edge data, corresponding to a reference edge image showing only edges, based on said reference image signal, and a laser edge data, corresponding to a laser edge image showing only edges, based on said laser image signal;

a second processing unit that detects a first partial edge shown only in one of said reference edge image and said laser edge image, based on said reference edge data and said laser edge data; and a third processing unit that generates normalized laser image data, by normalizing the luminance of said laser image with the luminance of said reference image, or normalized reference image data, by normalizing luminance of said reference image with the luminance of said laser image;

wherein said first processing unit generates said reference edge data and said laser edge data based on one of, said reference image signal and said normalized laser image data, and, said laser image signal and said normalized reference image data, and said second processing unit detects said first partial edge based on a difference of luminance in each pixel forming said reference edge image and said laser edge image.

14. An image data processor according to claim 13, wherein said third processing unit carries out a normalization process by making an average luminance of said laser image agree with an average luminance of said reference image, or the average luminance of said reference image agree with the average luminance of said laser image.

15. An image data processor according to claim 13, wherein said second processing unit detects said first partial edge by extracting only a pixel where said difference of luminance is one of a positive difference and a negative difference.

16. An image data processor according to claim 15, wherein said second processing unit detects a second partial edge, only in the other of said reference edge image and said laser edge image, by extracting a pixel where difference of luminance is the other of the positive difference and a negative difference.

17. An image data processor according to claim 13, wherein said second processing unit detects said first partial edge by extracting a pixel where the absolute difference of luminance in said reference edge image and said laser edge image is above a predetermined threshold value.

18. A computer that stores and executes a computer program, the computer comprising:

an image signal receiver that receives a reference image signal generated by an imaging device when said imaging device captures a reference image that is an optical image of an object illuminated by a reference light, and a laser image signal generated by said imaging device when said imaging device captures a laser image that is an optical image of said object illuminated by a laser light, said laser light having a shorter average wavelength than that of said reference light;

a generating processor that generates reference edge data corresponding to a reference edge image showing only edges, based on said reference image signal, and laser edge data corresponding to a laser edge image showing only edges, based on said laser image signal; and a detecting processor that detects a first partial edge only in one of said reference edge image and said laser edge image based on said reference edge data and said laser edge data; and a third processing unit that generates normalized laser image data, by normalizing the luminance of said laser image with the luminance of said reference image, or normalized reference image data, by normalizing luminance of said reference image with the luminance of said laser image;

wherein said generating processor generates said reference edge data and said laser edge data based on one of, said reference image signal and said normalized laser image data, and, said laser image signal and said normalized reference image data, and said detecting processor detects said first partial edge based on a difference of luminance in each pixel forming said reference edge image and said laser edge image.

19. An electronic endoscope system, comprising:

an electronic endoscope having an imaging device that generates a reference image signal when said imaging device captures an optical image of a required object illuminated by a reference light, and a laser image signal when said imaging device captures an optical image of said required object illuminated by a laser light, said laser light having a shorter average wavelength than that of said reference light;

a first processing unit that generates reference edge data corresponding to a reference edge image showing only edges, based on said reference image signal, and laser edge data corresponding to a laser edge image showing only edges, based on said laser image signal;

a second processing unit that detects a first partial edge only in one of said reference edge image and said laser edge image, based on said reference edge data and said laser edge data, and generates first partial edge data corresponding to a first partial edge image showing said first partial edge; and a monitor that displays said first partial edge image; and a third processing unit that generates normalized laser image data, by normalizing the luminance of said laser image with the luminance of said reference image, or normalized reference image data, by normalizing luminance of said reference image with the luminance of said laser image;

wherein said first processing unit generates said reference edge data and said laser edge data based on one of, said reference image signal and said normalized laser image data, and, said laser image signal and said normalized reference image data, and said second processing unit detects said first partial edge based on a difference of luminance in each pixel forming said reference edge image and said laser edge image.

* * * * *